(12) United States Patent
Song et al.

(10) Patent No.: US 12,391,952 B2
(45) Date of Patent: Aug. 19, 2025

(54) METHOD FOR SIMPLY CONSTRUCTING TWO-COMPONENT VIRAL VECTOR AND RELATED APPLICATIONS THEREOF

(71) Applicants: Institute of Cotton Research of the Chinese Academy of Agricultural Sciences, Anyang (CN); National Nanfan Research Institute (Sanya), Chinese Academy of Agricultural Sciences, Sanya (CN)

(72) Inventors: Guoli Song, Anyang (CN); Yunfei Hao, Anyang (CN); Dongyun Zuo, Anyang (CN); Hailiang Cheng, Anyang (CN); Ji Liu, Anyang (CN); Qiaolian Wang, Anyang (CN); Zhenhui Guan, Anyang (CN)

(73) Assignees: INSTITUTE OF COTTON RESEARCH OF THE CHINESE ACADEMY OF AGRICULTURAL SCIENCES, Anyang (CN); NATIONAL NANFAN RESEARCH INSTITUTE (SANYA), CHINESE ACADEMY OF AGRICULTURAL SCIENCES, Sanya (CN)

( * ) Notice: Subject to any disclaimer, the term of this patent is extended or adjusted under 35 U.S.C. 154(b) by 0 days.

(21) Appl. No.: 18/752,372

(22) Filed: Jun. 24, 2024

(65) Prior Publication Data

US 2025/0171793 A1 May 29, 2025

(30) Foreign Application Priority Data

Nov. 23, 2023 (CN) .......................... 202311569075.7

(51) Int. Cl.
C12N 15/82 (2006.01)
C12N 7/00 (2006.01)
C12N 15/66 (2006.01)

(52) U.S. Cl.
CPC .......... *C12N 15/8218* (2013.01); *C12N 7/00* (2013.01); *C12N 15/66* (2013.01); *C12N 15/8203* (2013.01); *C12N 2750/12021* (2013.01); *C12N 2750/12043* (2013.01); *C12N 2770/00021* (2013.01); *C12N 2770/00043* (2013.01)

(58) Field of Classification Search
None
See application file for complete search history.

(56) References Cited

U.S. PATENT DOCUMENTS 6,369,296 B1 4/2002 Ratcliff et al.

FOREIGN PATENT DOCUMENTS

WO WO0138513 A2 5/2001

OTHER PUBLICATIONS

BYJU's Biology, 2024.*
Tuttle, Plant Physiology, 2008, 148: 41-50.*
Sequence alignemnt-31, 2024.*
Sequence alignment-32, 2024.*
Zhang Jingxia et al., "Application of VIGS in Studies of Gene Function in Cotton", Cotton Science, Sep. 15, 2015, vol. 5, pp. 469-473, Abstract only.
Zhang Qinqin et al., "Application Advance of Virus-Induced Gene Silencing Technology in Dicotyledons", Journal of Henan Agricultural Sciences, vol. 2, Dec. 1, 2020, pp. 7-14, Abstract only.

* cited by examiner

*Primary Examiner* — Ileana Popa
(74) *Attorney, Agent, or Firm* — MUNCY, GEISSLER, OLDS & LOWE, P.C.

(57) ABSTRACT

A method for simply constructing a two-component virus vector and related applications. The two-component plant viral vector is optimized, so that a two-component virus genome is placed in a single plasmid. Due to the use of the single plasmid, the activation, resuspension and mixing processes of auxiliary bacteria are avoided, the workload of an *Agrobacterium* experimental stage is simplified by half, the potential cross-contamination risk in the bacteria mixing process is avoided, and the virus infectivity is improved, so that the use of the two-component viral vector is greatly simplified.

1 Claim, 4 Drawing Sheets

Specification includes a Sequence Listing.

METHOD FOR SIMPLY CONSTRUCTING TWO-COMPONENT VIRAL VECTOR AND RELATED APPLICATIONS THEREOF

REFERENCE TO AN ELECTRONIC SEQUENCE LISTING

The content of the electronic sequence listing (SEQUENCE-0213-0319PUS1. xml; Size: 33,468 bytes; and Date of Creation: Jun. 24, 2024) is herein incorporated by reference in its entirety.

TECHNICAL FIELD

This application belongs to the technical field of bioengineering, and specifically relates to a method for simply constructing a two-component viral vector and related applications thereof.

BACKGROUND

Plant viral vectors are a special type of plant expression vectors that are often used in virus-induced gene silencing (VIGS) experiments. Compared with ordinary plant expression vectors, the viral vectors have unique advantages in studying plant gene functions. The principle is as follows: according to characteristics that plants have RNAi immune response to viruses and the plant viruses may replicate in the plants and systematically infect the plants, endogenous gene fragments or full lengths can be expressed through plant viral vectors, thereby achieving virus-mediated gene silencing (VIGS), virus-mediated gene overexpression (VOX), virus-induced flowering (VIF), and virus-mediated gene editing (VIGE), etc.

At present, relatively few viral vectors have been modified and used to study plant gene functions, mainly some RNA viruses and a few DNA viruses. Among them, a single-stranded linear RNA virus TRV has become the most widely used viral vector due to its wide host range. The TRV virus contains two genomic components, which are placed into two plasmids pTRV1 and pTRV2. When a TRV system is used, a target fragment needs to be constructed at the multiple cloning site of pTRV2, and then the two plasmids are mixed and delivered to plant cells. The TRV virus on the plasmid is transcribed by the 35S expression cassette, so the viral activity can be restored after entering plant cell transcription. The two-component circular DNA virus CLCrV is a widely used viral vector in cotton. Its vector system includes two genomes, pCLCrVA and pCLCrVB (hereinafter referred to as pVA and pVB). When a CLCrV system is used, the target fragment needs to be constructed at the multiple cloning site of VA, and then the two plasmids are mixed and delivered to the plant cells. CLCrV viral coding components on the plasmid are flanked by their respective CR regions (conservative regions containing splicing sites). When viral replicase is expressed, the linear CLCrV viral components will be spliced to re-form circular VA and VB genomes, so as to restore the viral activity. It is worth noting that the VA multiple cloning site contains a coding frame of viral proteins, so gene overexpression can be achieved by placing exogenous genes in the coding frame. In the past, the optimization of TRV viral vectors mainly focused on optimizing the multiple cloning site region of pTRV2 plasmid to improve the vector construction mode, while the optimization of CLCrV viral vectors mainly changed from gene gun to *Agrobacterium* infection. In addition, there are still optimizations on the conditions of *Agrobacterium* infection such as temperature and a formula of a resuspension. At present, there are no related reports in constructing the viral vectors with multiple genomic components into a single plasmid system.

The current mainstream method of using plant viral vectors is to deliver them into plant cells across cell barriers through *Agrobacterium*. Therefore, the use of the plant viral vectors is mainly divided into three steps: plasmid construction, *Agrobacterium* transformation and infection. Since the above two types of viral vectors are two-component systems, the infection steps require additional activation, shaking, and resuspension of the auxiliary bacteria (carrying the plasmid pTRV1 or pCLCrVB) and a mixing step of main bacteria (carrying the plasmid pTRV2 or pCLCrVA). This process greatly increases the workload of the infection step and increases the risk of cross-contamination of a bacterial solution. When high-throughput experiments are required, the complexity of experimental operations and the risk of contamination increase significantly. On the other hand, there is currently little development of new viral vectors in the field of botany. Due to their host specificity and effectiveness, two-component viral vectors are often not easily replaced by new viral vectors in scientific research applications. Therefore, their simplified transformation has extremely high application value.

SUMMARY

In view of this, the present disclosure provides a method for simply preparing a two-component plant viral vector and related applications thereof. In view of the replication characteristics of two-component DNA and RNA viruses, according to the present disclosure, the two-component virus genomes are concatenated and transformed into a single plasmid system, which greatly simplifies experimental operations and effectively avoids potential experimental contamination.

In order to achieve the above objects, the present disclosure provides the following technical solutions.

The present disclosure provides a pair of adapter sequences, the adapter sequences including sequences shown in SEQ ID NO.31 and SEQ ID NO.32. As a result, the VIGS vectors for multiple viruses of one gene through a single PCR product can be simply and rapidly constructed. In an actual operation, the present disclosure reserves the adapter sequences in advance to facilitate subsequent replacement of a target gene.

The present disclosure also provides a method for simply constructing a two-component viral vector, including the following steps: modifying a viral vector skeleton and constructing plasmid series of a two-component virus;

the modifying a viral vector skeleton includes the following steps:
analyzing and obtaining an enzyme cutting site at a multiple cloning site, and modifying the enzyme cutting site at the multiple cloning site in the viral vector skeleton into a restriction endonuclease or exonuclease enzyme cutting site in a multiple cloning site region;
a flanking sequence of the enzyme cutting site is modified into the above-mentioned adapter sequence;
the constructing plasmid series of the two-component virus includes the following steps:
concatenating the adapter sequences through PCR and homologous recombination to obtain a single plasmid of the two-component viral vector.

The present disclosure also provides an application of the above-mentioned adapter sequences or the above-mentioned method of simplified construction in completing the construction of multiple viral vectors through one PCR product.

The present disclosure provides two VIGS plasmids: pVS and pVS2. Usually, DNA virus and RNA viral vectors have different multiple cloning sites, and the construction of multiple viral vectors cannot be completed through one PCR product. In the present disclosure, the multiple cloning site adapter sequences as same as the pVS plasmid based on CLCrV virus are introduced into the pVS2 plasmid based on TRV virus, and thus can be used to construct gene silencing plasmids of the two viruses at the same time.

The present disclosure provides a two-component DNA viral vector, and the method for preparing the two-component DNA viral vector is as shown above;
when the two-component DNA viral vector is a circular DNA virus, the two components in the two-component DNA viral vector are flanked by respective CR regions, the CR regions may be linked by any enzyme cutting site sequence, and the other end of the CR region is linked to a T-DNA border of the plasmid or other prokaryotic expression components; and the CR region comprises a conserved splicing site during viral replication.

The present disclosure provides a two-component RNA viral vector, and the method for preparing the two-component RNA viral vector is as shown above;
when the two-component RNA viral vector is a linear RNA virus, the two components of the two-component RNA viral vector are placed in two expression cassettes for independent expression; each of the expression cassettes is a 35S expression cassette, a promoter is 35S, and a terminator is NOS. The application preferably includes denovo development of vectors for multi-component viruses that have not been vectorized.

In view of the replication characteristics of the two-component circular DNA virus, the two genomes of the virus only need to be placed into the T-DNA border in any direction and order; the two genomes of a two-component RNA virus need to be placed into two different eukaryotic gene expression cassettes for transcription. Preferably, the DNA virus is CLCrV and the RNA virus is TRV.

The present disclosure provides an application of the above-mentioned two-component DNA viral vector and/or the above-mentioned two-component RNA viral vector in *Agrobacterium* infection.

In the present disclosure, the *Agrobacterium* infection further includes downstream applications of viral vectors; and the downstream applications include VIGS, VOX, VIGE, and VIF.

Based on the technical solution provided above, the present disclosure provides a method for concatenating multiple viral genome modules into a single plasmid, which can more easily use viral vectors to perform complex genetic manipulation. The usual method for combining viral vectors for gene manipulation is to inject a mixture of *Agrobacterium* containing different gene-manipulating viral plasmids. The present disclosure provides a more modular way to achieve complex genetic manipulation by concatenating multiple viral genomes in the single plasmid to achieve specific application purposes.

The beneficial effects of the present disclosure are as follows: when the genomes of the two-component virus are concatenated and modified into a single plasmid system, it cannot only simplify experimental operations and avoid experimental contamination, but also improve the infectivity of the virus and increase the success rate of the experiment. Single-plasmid viral vectors containing two components or multiple components are also suitable for high-throughput experiments, such as VIGS mutant libraries and VIF-based large-scale material rapid seed reproduction and the like. A flow chart for the use of simplified DNA and RNA viral vectors is shown in FIG. 1.

BRIEF DESCRIPTION OF DRAWINGS

Figure 1:
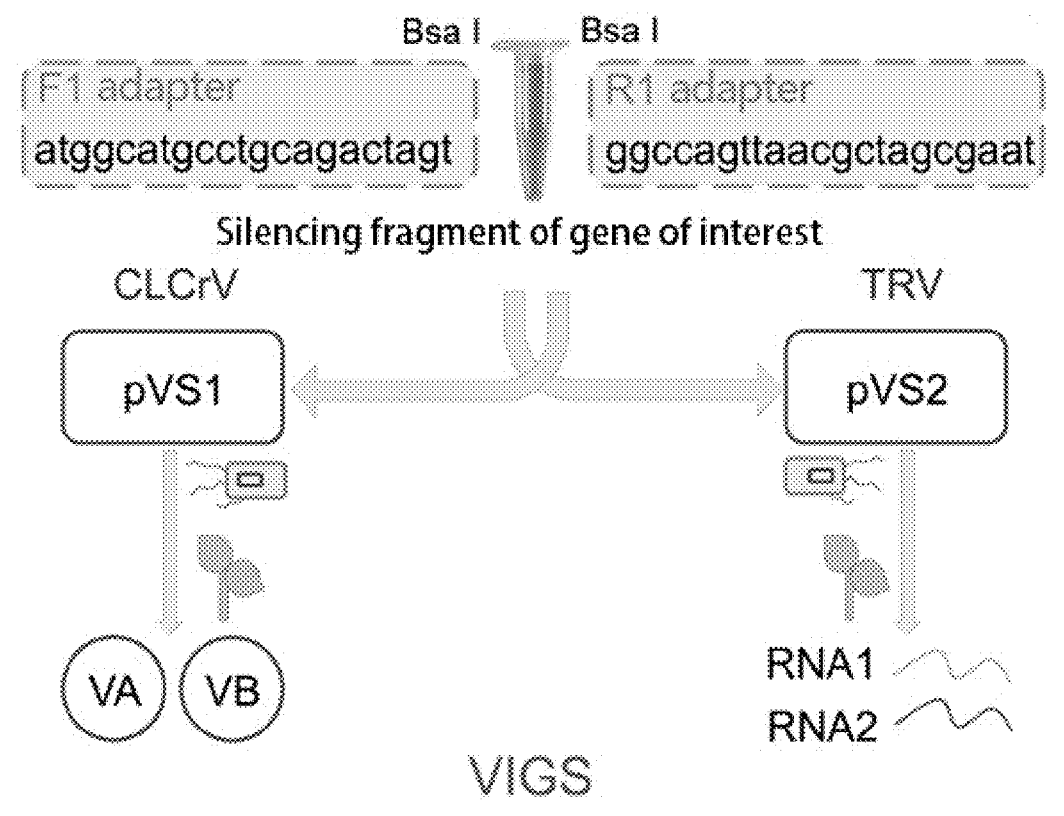

FIG. 1 is a flow chart for use of simplified DNA and RNA viral vectors.

FIG. 4 shows simultaneously overexpression of an SFT gene and silencing of an SP gene by using the VS1 system concatenated by a plurality of VA genome;

FIG. 5 shows a PCR identification results of a bacterial solution in Example 4.

DETAILED DESCRIPTION

Figure 2:
FIG. 2 shows an albino phenotype of a plant with PDS gene silencing after successfully silencing a cotton PDS gene by using a VS1 system.

The present application will be further explained below in conjunction with Examples.

Example 1

A method for simplifying a two-component DNA virus—CLCrV vector

In this example, a simplifying process of the two-component DNA virus is illustrated by taking the two-component virus-CLCrV as an example. Whether the simplified plasmid works normally is determined through a VIGS phenotype result of a cotton PDS gene after *Agrobacterium* infection.

A specific implementation process is briefly introduced below.

(1) Modification of a Viral Vector Skeleton

Through two rounds of plasmid point mutation experiments, a Bsa I enzyme cutting site on a pVA plasmid was mutated sequentially and a 35S expression cassette was deleted.

Point mutation primers used are as follows:

```
clcrv M-BSA F:
5'-GGAAAGACACCTTTTCGACCTTTTTCCCCT-3',
SEQ ID NO. 1;

clcrv M-Bsa R:
5'-AAAAGTGTCTTTCCTGTGGATAGCACGTACAT-3',
SEQ ID NO. 2;

clcrv-D-HygR F:
5'-TAATTCGGGGATAGCCCTTTGGTCTTCTGAGACTGT-3',
SEQ ID NO. 3;

clcrv-D-HygR R:
5'-CAAAGGGCTATCCCGAATTAATTCGGCGTTAATTCA-3',
SEQ ID NO. 4.
```

A PCR reaction system is shown in Table 1, and a PCR amplification program is shown in Table 2.

TABLE 1

PCR reaction system

| Component | Volume |
|---|---|
| Phanta Max Super-Fidelity DNA Polymerase | 1 μL |
| 2 × Phanta Max Buffer | 10 μL |
| dNTP Mix | 0.5 μL |
| Upstream primer | 0.8 μL |
| Downstream primer | 0.8 μL |
| Template DNA | 1 μL |
| Supplementing double distilled water to | 20 μL |

TABLE 2

PCR Amplification program

| Step | Temperature | Time | Cycle number |
|---|---|---|---|
| Predenaturation | 95° C. | 5 min | 1 |
| Denaturation | 95° C. | 15 sec | 33 |
| Annealing | 58° C. | 15 sec | |
| Extension | 72° C. | 8 min | |
| Extension | 72° C. | 5 min | 1 |

Further, after the amplified PCR product was purified, 1 μL of Dpn I was added and placed at 37° C. to digest the template plasmid for 2 hours.

Further, a linear PCR product was recombined by using a ClonExpress® II One Step Cloning Kit.

Further, a recombinant product was transformed and entered into *E. coli* strain DH5α. After overnight growth on a plate, monoclones were selected for colony PCR identification and positive transformants were screened.

Further, whether the point mutation was successful was confirmed by a method of a Sanger sequencing. The plasmid that was finally sequenced was named pMDA.

(2) Construction of Plasmid Series of the Two-Component Virus

Through two rounds of vector construction, the plasmid series for constructing the two-component virus was obtained. First, a silencing fragment of a cotton PDS gene was constructed into a multiple cloning site of pMDA to obtain a pMDA-PDS plasmid, and then VB was constructed into the pMDA-PDS plasmid to obtain pMDAB-PDS (hereinafter referred to as pVS-PDS).

The PCR amplification primers used are as follows:

```
clcrv-PDS F:
5'-AACGCTAGCGAATTCACTAGTGCCTGAAGACTGGAG-3',
SEQ ID NO. 5;

clcrv-PDS R:
5'-GGCATGCCTGCAGACTAGTGCTTTACTCTGATCC-3',
SEQ ID NO. 6;

Clone VB F:
5'-AACCTATCCCAAGTGGAGCTCCGGGGGATCCACTAGTAAAC-3',
SEQ ID NO. 7;

Clone VB R:
5'-CATGATTACGAATTCGAGCTCATTCGAGCTCCAGAACGATC-3',
SEQ ID NO. 8.
```

The PCR reaction system is shown in Table 3, and the PCR amplification program is shown in Table 4.

TABLE 3

PCR reaction system

| Component | Volume |
|---|---|
| Phanta Max Super-Fidelity DNA Polymerase | 1 μL |
| 2 × Phanta Max Buffer | 10 μL |
| dNTP Mix | 0.5 μL |
| Upstream primer | 0.8 μL |
| Downstream primer | 0.8 μL |
| Template DNA | 1 μL |
| Supplementing double distilled water to | 20 μL |

TABLE 4

PCR amplification program

| Step | Temperature | Time | Cycle number |
|---|---|---|---|
| Predenaturation | 95° C. | 5 min | 1 |
| Denaturation | 95° C. | 15 sec | 33 |
| Annealing | 58° C. | 15 sec | |
| Extension | 72° C. | 2 min | |
| Extension | 72° C. | 5 min | 1 |

The amplified PCR products were recovered by using an agarose gel DNA recovery kit (enhanced type).

The vectors used in the two rounds of experiments were linearized by using restriction enzymes SpeI and SacI.

The enzyme cutting system is shown in Table 5.

TABLE 5

Enzyme cutting system

| Component | Volume |
|---|---|
| 10 × Cut smart buffer | 10 μL |
| SpeI/Sac I | 1 μL |
| Vector | 2000 ng |
| Supplementing double distilled water to | 100 μL |

The reaction system was placed in a 37° C. incubator for enzyme cutting overnight.

Further, an ultra-thin DNA product purification kit was used to recover the linearized vector.

Further, the PCR product and linearized vector were recombined by using a ClonExpress® II One Step Cloning Kit.

Further, a recombinant product was transformed and entered into *E. coli* strain DH5α. After overnight growth on a plate, monoclones were selected for colony PCR identification and positive transformants were screened.

Further, whether the PCR fragment was successfully constructed was confirmed by a method of a Sanger sequencing. The final plasmid is pVS-PDS.

(3) *Agrobacterium* Infection

Since the VA and VB genomes of the CLCrV virus were placed in a single plasmid, and the plasmid contained the silencing fragment of cotton PDS, whether the simplified method was successful could be determined by way of whether cotton cotyledons infected by the pVS-PDS *Agrobacterium* were whitened.

Further, pVS-PDS was transformed and entered into *Agrobacterium* GV3101 through heat shock transformation.

Further, after the plate grew on kana and rifampicin double-resistant plates for two days, monoclones were selected for colony PCR identification and positive transformants were screened.

Further, positive monoclones were selected and shook overnight until the OD value was 0.5-1.0.

Further, the bacteria solution was collected at the bottom of a centrifuge tube by centrifugalization at 6000 rpm for 10 minutes, a supernatant was discarded, and the mixture was adjusted with a resuspending solution till OD=0.5-1.0.

A formula of the resuspending solution is shown in Table 6.

TABLE 6

Formula of the resuspending solution

| Resuspending solution | 100 mL |
|---|---|
| MgCl2 (1M) | 1 mL |
| MES(0.5M) | 2 mL |
| AS (100 mM) | 200 μL |

Further, after standing for 3 hours in the dark, pores were punched to inject the resuspending solution on the back of the flat cotyledons of cotton at a cotyledonary stage.

Further, after being kept in the dark for 12 h, the mixture was cultured in a 25-28° C. culture room.

As shown in FIG. 2, the silencing phenotype of pVS-PDS-injected plants can last until the later stages of cotton growth and development, and obvious albino phenotypes can be seen in leaves, stems, and bracts. The above results show that the simplification of the two-component DNA virus-CLCrV vector is successful.

Example 2

Method for Simplifying Two-Component RNA Virus-TRV Vector

In this example, a two-component virus-TRV was used as an example to illustrate the simplification process of the two-component RNA virus. Whether the simplified single plasmid can work normally is determined by the VIGS phenotype results of the CLA gene of new cotton leaves after *Agrobacterium* infection.

A specific implementation process is briefly introduced below.

(1) Modification of a Viral Vector Skeleton

Since the viral component on the pTRV1 plasmid contained five dispersed Bsa I enzyme cutting sites, all Bsa I enzyme cutting sites on the pTRV1 plasmid were synonymously mutated through staged gene synthesis and vector construction by a gene synthesis company. Then, the resistance selection gene BlpR in the 35S expression cassette was deleted by BamHI enzyme cutting, and two concatenated Bsa Is were introduced by gene synthesis for subsequent concatenated pTRV2 plasmids. The gene fragments synthesized in stages were shown in SEQ ID NO. 9. SEQ ID NO. 10 and SEQ ID NO. 11. Synthetic fragments used for intermediate plasmid construction was shown in SEQ ID NO. 12. The final intermediate plasmid was named 2_3_2_1_VIGS pYL192 (TRV1).

SEQ ID NO. 9:
GTTATTGCTTTTAGATAGAGTTCCTGCTCTGCAAGAGGTGGATGACATCG

GTGGTCAATGGTCGTTTTGGGTAACTAGAGGTGAGAAAAGGATTCATTCC

TGTTGTCCAAATCTAGATATTCGGGATGATCAGAGAGAAATTTCTCGACA

GATATTTCTTACTGCTATTGGTGATCAAGCTAGAAGTGGTAAGAGACAGA

TGTCGGAGAATGAGCTGTGGATGTATGACCAATTTCGTGAAAATATTGCT

GCGCCTAACGCGGTTAGGTGCAATAATACATATCAGGGTTGTACATGTAG

GGGTTTTTCTGATGGTAAGAAGAAAGGCGCGCAGTATGCGATAGCTCTTC

ACAGCCTGTATGACTTCAAGTTGAAAGACTTGATGGCTACTATGGTTGAG

AAGAAAACTAAAGTGGTTCATGCTGCTATGCTTTTTGCTCCTGAAAGTAT

GTTAGTGGACGAAGGTCCATTACCTTCTGTTGACGGTTACTACATGAAGA

AGAACGGGAAGATCTATTTCGGTTTTGAGAAAGATCCTTCCTTTTCTTAC

ATTCATGACTGGGAAGAGTACAAGAAGTATCTACTGGGGAAGCCAGTGAG

TTACCAAGGGAATGTGTTCTACTTCGAACCGTGGCAGGTGAGAGGAGACA

CAATGCTTTTTTCGATCTACAGGATAGCTGGAGTTCCGAGGAGGTCGCTA

TCATCGCAAGAGTACTACCGAAGAATATATATCAGTAGATGGGAAAACAT

GGTTGTTGTCCCAATTTTCGATCTGGTCGAATCAACGCGAGAGTTGGTCA

AGAAAGACCTGTTTGTAGAAACAATTCATGGACAAGTGTTTGGATTACAT

AGCTAGGTTTATCTGACCAGCAGCTGACCATAAGCAATGTTAAATCATAC

TTGAGTTCAAATAATTGGGTCTTATTCATAAACGGGGCGGCCGTGAAGAA

CAAGCAAAGTGTAGATTCTCGAGATTTACAGTTGTTGGCTCAAACTTTGC

TAGTGAAGGAACAAGTGGCGCGACCTGTCATGAGGGAGTTGCGTGAAGCA

ATTCTGACTGAGACGAAACCTATCACGTCATTGACTGATGTGCTGGGTTT

AATATCAAGAAACTGTGGAAGCAGTTTGCTAACAAGATCGCAGTCGGCG

GATTCGTTGGCATGGTTGGTACTCTAATTGGATTCTATCCAAAGAAGGTA

CTAACCTGGGCGAAGGACACACCAAATGGTCCAGAACTATGTTACGAGAA

CTCGCACAAAACCAAGGTGATAGTATTTCTGAGTGTTGTGTATGCCATTG

GAGGAATCACGCTTATGCGTCGAGACATCCGAGATGGACTGGTGAAAAA

ACTATGTGATATGTTTGATATCAAACGGGGGGCCCATGTCTTAGACGTTG

AGAATCCGTGCCGCTATTATGAAATCAACGATTTCTTTAGCAGTCTGTAT

TCGGCATCTGAGTCCCGGTGAGACG;

SEQ ID NO. 10:
TGCCGCGCTTACGAAGGCGGCTTTGGCAAGATTTTTTGTTACTGAGACGG

TCTTATGACGGTTTCGGTCTAGGTTTGATGTCTTTAGACATCATGAAGGG

CCTTGCG;

SEQ ID NO. 11:
GCCGAAGTATTTTCACAGAAGAAGAGAAACTGTCCTAAATCATGTTGGTG

GGAAGAAGAGTGAACACAAGTTAGACGTTTTTGACCAAAGGGATTACAAA

ATGATTAAATCTTACGCGTTTCTAAAGATAGTAGGTGTACAATTG;

SEQ ID NO. 12:
GGATCCCAGGAAACAGCTATGACCAATTCCCGATCTAGTAACATAGATGA

CACCGCGCGCGATAATTTATCCTAGTGAGACCGTAGGTCTCATTCTACTG

CGATCACTGACATACCCCAGCCAGGGCAACACCATAGGTGCAATGTTTTT

ATCCTCTCCAAATGAAATGAACTTCCTTATATAGAGGAAGGGTCTTGCGA

AGGATAGTGGGATTGTGCGTCATCCCTTACGTCAGTGGAGATG.

On the other hand, in order to use the same PCR product to construct TRV and CLCrV vectors at the same time, the adapter sequence on the pTRV2 plasmid was replaced to be exactly the same as CLCrV, and the same Bsa I enzyme cutting strategy as CLCrV was used at the multiple cloning site.

The adapter and enzyme cutting site sequences were introduced into both ends of the CLA gene through overlap extension PCR amplification.

The primers used in overlap extension PCR are as follows:

V2 F1:
5'-CTTTGGAAGAAGACTTGTACACTTATTACAAATTCGAT-3',
SEQ ID NO. 13;

V2 R1:
5'-TCCTTAAATCCCTAAAGCTTGGGATTAGGACGTATCGGACCTC-3',
SEQ ID NO. 14;

V2 F2:
5'-AAGCTTAGGGATTTAAGGACGTGAACTCTGTTGA-3',
SEQ ID NO. 15;

V2 R2:
5'-ATTCGCTAGCGTTAACTGGCCAATTCGGTAACCTTACTCACAGAATC
TAA GTC-3', SEQ ID NO. 16;

V2 F3:
5'-GCCAGTTAACGCTAGCGAATCGAGACCGCCCTTTGTGCATCTTCATT
TCC T-3', SEQ ID NO. 17;

V2 R3:
5'-GGGACATGCCCGGGCCTCGAATGGCATGCCTGCAGACTAGTTGAGAC
CATTAACACCGTTGCGGCTAAGC-3', SEQ ID NO. 18.

The PCR reaction system is shown in Table 7, and the PCR amplification program is shown in Table 8.

TABLE 7

PCR reaction system

| Component | Volume |
| --- | --- |
| Phanta Max Super-Fidelity DNA Polymerase | 1 μL |
| 2 × Phanta Max Buffer | 10 μL |
| dNTP Mix | 0.5 μL |
| Upstream primer | 0.8 μL |
| Downstream primer | 0.8 μL |
| Template DNA | 1 μL |
| Supplementing double distilled water to | 20 μL |

TABLE 8

PCR amplification program

| Step | Temperature | Time | Cycle number |
| --- | --- | --- | --- |
| Predenaturation | 95° C. | 5 min | 1 |
| Denaturation | 95° C. | 15 sec | 33 |
| Annealing | 58° C. | 15 sec | |
| Extension | 72° C. | 1 min | |
| Extension | 72° C. | 5 min | 1 |

Further, the amplified overlap extension PCR product was purified.

Further, the pTRV2 plasmid was linearized by BsrG I and Xho I.

The enzyme cutting system is shown in Table 9.

TABLE 9

Enzyme cutting system

| Component | Volume |
| --- | --- |
| 10 × Cut smart buffer | 10 μL |
| SpeI/Sac I | 1 μL |
| Vector | 2000 ng |
| Supplementing double distilled water to | 100 μL |

The reaction system was placed in a 37° C. incubator for enzyme cutting overnight.

Further, the PCR product and linearize the pTRV2 plasmid were recombined by using a ClonExpress® II One Step Cloning Kit.

Further, a recombinant product was transformed and entered into *E. coli* strain EPI300. After overnight growth on a plate, monoclones were selected for colony PCR identification and positive transformants were screened.

Further, whether the modification of pTRV2 was successful was confirmed by a method of a Sanger sequencing. The finally modified pTRV1 and pTRV2 plasmids were named 2_3_2_1_VIGS pYL192 (TRV1) and V2-CLA-Bsa I respectively.

(2) Construction of Plasmid Series of Two-Component Virus

The viral component on the V2-CLA-Bsa I plasmid was amplified by PCR.

The PCR amplification primers used are as follows:

Clone V2 F:
5'-TGTCAGTGATCGCAGTAGAATGTACTAATT-3',
SEQ ID NO. 19;

Clone V2 R:5'-CGCGCGATAATTTATCCTAGTTTGCG-3',
SEQ ID NO. 20.

The PCR reaction system is shown in Table 10, and the PCR amplification program is shown in Table 11.

TABLE 10

PCR reaction system

| Component | Volume |
| --- | --- |
| Phanta Max Super-Fidelity DNA Polymerase | 1 μL |
| 2 × Phanta Max Buffer | 10 μL |
| dNTP Mix | 0.5 μL |
| Upstream primer | 0.8 μL |
| Downstream primer | 0.8 μL |
| Template DNA | 1 μL |
| Supplementing double distilled water to | 20 μL |

TABLE 11

PCR amplification program

| Step | Temperature | Time | Cycle number |
| --- | --- | --- | --- |
| Predenaturation | 95° C. | 5 min | 1 |
| Denaturation | 95° C. | 15 sec | 33 |
| Annealing | 58° C. | 15 sec | |
| Extension | 72° C. | 2 min | |
| Extension | 72° C. | 5 min | 1 |

The amplified PCR products were recovered by using an agarose gel DNA recovery kit (enhanced type).

An intermediate plasmid 2_3_2_1_VIGS pYL192 (TRV1) was linearized by using a restriction enzyme Bsa I. The enzyme cutting system is shown in Table 12.

TABLE 12

Enzyme cutting system

| Component | Volume |
| --- | --- |
| 10 × Cut smart buffer | 10 μL |
| Bsa I | 1 μL |
| Vector | 2000 ng |
| Supplementing double distilled water to | 100 μL |

The reaction system was placed in a 37° C. incubator for enzyme cutting overnight.

Further, the linearized vector was recovered by an ultra-thin DNA product purification kit.

Further, the PCR product and linearized vector were recombined by using a ClonExpress® II One Step Cloning Kit.

Further, a recombinant product was transformed and entered into *E. coli* strain EPI300. After overnight growth on a plate, monoclones were selected for colony PCR identification and positive transformants were screened.

Further, a Sanger sequencing method was performed by using bacterial liquid PCR products to confirm positive clones. Whether the concatenated plasmid was successfully constructed was finally confirmed by next-generation sequencing of the entire plasmid. The final plasmid was named pVS2-CLA.

(3) *Agrobacterium* Infection

Since the RNA1 and RNA2 genomes of the TRV virus were placed in a single plasmid, and the plasmid contained the silencing fragment of cotton CLA, whether the simplified method was successful could be determined by way of whether cotton cotyledons infected by the pVS2-CLA *Agrobacterium* were whitened.

Further, pVS2-CLA was transformed and entered into *Agrobacterium* GV3101 through heat shock transformation.

Further, after the plate grew on kana and rifampicin double-resistant plates for two days, monoclones were selected for colony PCR identification and positive transformants were screened.

Further, positive monoclones were selected and shook overnight until the OD value was 0.5-1.0.

Further, a bacteria solution was collected at the bottom of a centrifuge tube by centrifugalization at 6000 rpm for 10 minutes, a supernatant was discarded, and the mixture was adjusted with the resuspending solution till OD=0.1-0.3.

A formula of the resuspending solution is shown in Table 13.

TABLE 13

Formula of the resuspending solution

| Resuspending solution | 100 mL |
| --- | --- |
| MgCl2 (1M) | 1 mL |
| MES(0.5M) | 2 mL |
| AS (100 mM) | 200 μL |

Further, after standing for 3 hours in the dark, pores were punched to inject the resuspending solution to the back of the flat cotyledon of cotton at a cotyledonary stage.

Further, after being kept in the dark for 12 h, the mixture was cultured in a culture room at 25° C. or below.

Figure 3:
FIG. 3 shows an albino phenotype of a plant with PDS gene silencing after successfully silencing a cotton CLA gene by using a VS2 system.

As shown in FIG. 3, 2 weeks after injection, the plants injected with pVS2-CLA turned completely white above the cotyledon node, indicating that the CLA gene is successfully silenced. Therefore, the simplification of the two-component RNA virus-TRV vector was successful. When the two-component RNA viral vector was used in cotton, the concentration of the bacteria solution was OD=0.3.

Example 3

Simultaneous Implementation of VIGS, VOX, and VIF by Using a Simplified Two-Component Viral Vector.

Figures 4, 5:
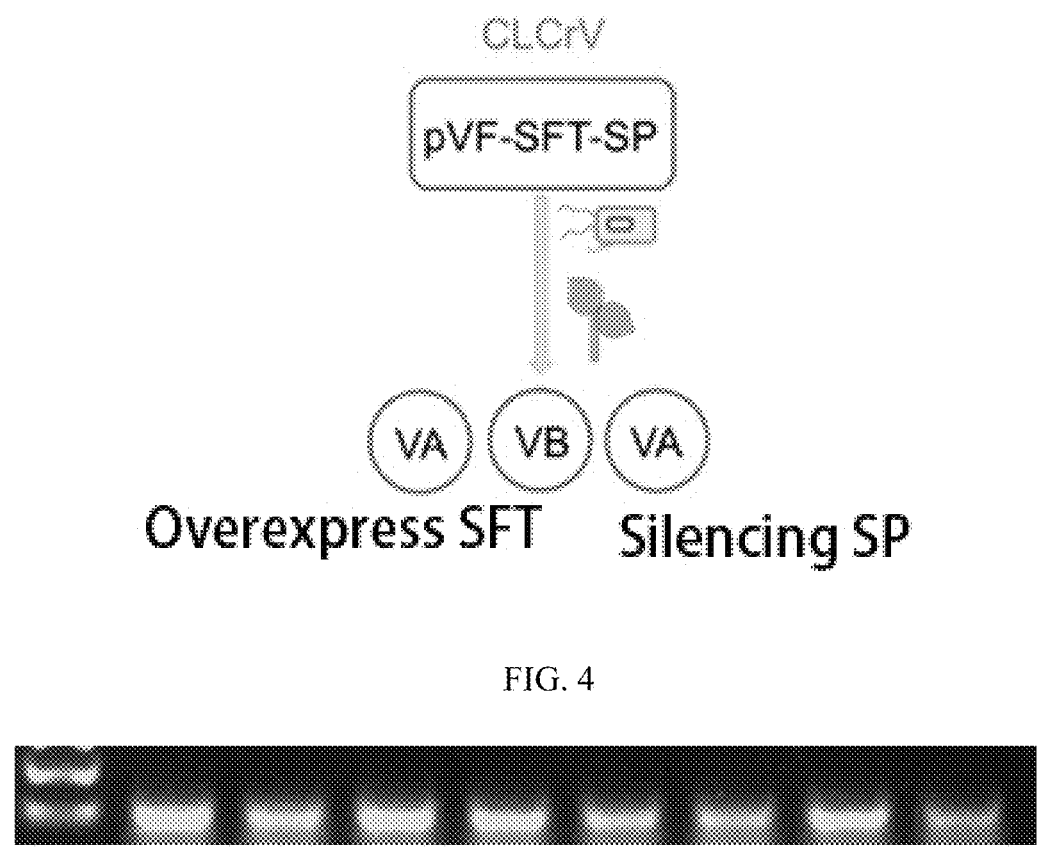

In this example, two plasmids, pVF-SFT and pVS-SP, were first constructed to overexpress an SFT gene and silence the SP gene respectively. Using these two plasmids as templates, a plasmid pVF-SFT-SP was obtained by way of overlap extension PCR. The two VA genomes in the pVF-SFT-SP plasmid shared the same CR region, thereby ensuring that both VA genomes could restore circularity. In addition, an empty pVSe containing no endogenous gene fragments was constructed as a negative control, and whether the three-component single plasmid system could successfully overexpress the SFT gene and silence the SP gene was verified by using the qRT-PCR results and flowering time phenotypes, and thus VIGS, VOX, and VIF were implemented simultaneously. The schematic diagram is shown in FIG. 4.

A specific implementation process is briefly introduced below.

(1) Construction of Two Plasmids, pVF-SFT and pVS-SP

The primers used were as follows:

```
VF-SFT F:
5'-ATGGCATGCCTGCAGACTAGTATGCCTAGAGATAGAGATCCTTTGG
TT G-3', SEQID NO. 21;

VF-SFT R:
5'-GGCCAGTTAACGCTAGCGAATTCATGTCCTACGGCCACCGG-3',
SEQ ID NO. 22;

VS GHSP F:
5'-ATGGCATGCCTGCAGACTAGTGCGTCTTCTAGCAGCTGTTTCC
C-3', SEQ ID NO. 23;

VS GHSP R:
5'-GGCCAGTTAACGCTAGCGAATGAGTGATTGGGGATGTTATTGATG
CCC-3', SEQ ID NO. 24.
```

The PCR reaction system is shown in Table 14, and the PCR amplification program is shown in Table 15.

TABLE 14

PCR reaction system

| Component | Volume |
| --- | --- |
| Phanta Max Super-Fidelity DNA Polymerase | 1 μL |
| 2 × Phanta Max Buffer | 10 μL |
| dNTP Mix | 0.5 μL |
| Upstream primer | 0.8 μL |
| Downstream primer | 0.8 μL |
| Template DNA | 1 μL |
| Supplementing double distilled water to | 20 μL |

TABLE 15

PCR amplification program

| Step | Temperature | Time | Cycle number |
|---|---|---|---|
| Predenaturation | 95° C. | 5 min | 1 |
| Denaturation | 95° C. | 15 sec | 33 |
| Annealing | 58° C. | 15 sec | |
| Extension | 72° C. | 1 min | |
| Extension | 72° C. | 5 min | 1 |

The amplified PCR products were recovered by using an agarose gel DNA recovery kit (enhanced type).

The pVS vector was linearized by using a restriction enzyme BsaI.

An enzyme cutting system is shown in Table 16. In Table 16, the volume of the component 10× Cut smart buffer is 10 μL, the volume of the component BsaI is 1 μL, and the volume of the component carrier is 2000 ng. Finally, double distilled water is supplemented to 100 μL.

TABLE 16

Enzyme cutting system

| Component | Volume |
|---|---|
| 10 × Cut smart buffer | 10 μL |
| BsaI | 1 μL |
| Vector | 2000 ng |
| Supplementing double distilled water to | 100 μL |

The reaction system was placed in a 37° C. incubator for enzyme cutting overnight.

Further, the linearized vector was recovered by an ultra-thin DNA product purification kit.

Further, the PCR product and linearized vector were recombined by using a ClonExpress® II One Step Cloning Kit.

Further, a recombinant product was transformed and entered into *E. coli* strain DH5α. After overnight growth on a plate, monoclones were selected for colony PCR identification and positive transformants were screened.

Further, whether the PCR fragment was successfully constructed was confirmed by a method of a Sanger sequencing. The final plasmids obtained were pVF-SFT and pVS-SP.

(2) Construction of pVF-SFT-SP Plasmid

The primers used are as follows:

VS GHSP F:
5'-ATGGCATGCCTGCAGACTAGTGCGTCTTTCTAGCAGCTGTTTCCC-3', SEQ ID NO. 25;

VF R1:
5'-CTAGGCTAGTCAGGCGCAAAATGAT-3', SEQ ID NO. 26;

VF F1:
5'-ATCATTTTGCGCCTGACTAGCCTAG-3', SEQ ID NO. 27;

VF-SFT R:
5'-GGCCAGTTAACGCTAGCGAATTCATGTCCTACGGCCACCGG-3', SEQ ID NO. 28.

The first two primers were used to amplify the SP silent fragment and CR region, and the last two primers were used to amplify the full-length cDNA of SFT.

The PCR reaction system is shown in Table 17, and the PCR amplification program is shown in Table 18.

TABLE 17

PCR reaction system

| Component | Volume |
|---|---|
| Phanta Max Super-Fidelity DNA Polymerase | 1 μL |
| 2 × Phanta Max Buffer | 10 μL |
| dNTP Mix | 0.5 μL |
| Upstream primer | 0.8 μL |
| Downstream primer | 0.8 μL |
| Template DNA | 1 μL |
| Supplementing double distilled water to | 20 μL |

TABLE 18

PCR amplification program

| Step | Temperature | Time | Cycle number |
|---|---|---|---|
| Predenaturation | 95° C. | 5 min | 1 |
| Denaturation | 95° C. | 15 sec | 33 |
| Annealing | 58° C. | 15 sec | |
| Extension | 72° C. | 2 min | |
| Extension | 72° C. | 5 min | 1 |

The amplified PCR products were recovered by using an agarose gel DNA recovery kit (enhanced type).

A pVS vector was linearized by using a restriction enzyme BsaI.

An enzyme cutting system is shown in Table 19.

TABLE 19

Enzyme cutting system

| Component | Volume |
|---|---|
| 10 × Cut smart buffer | 10 μL |
| BsaI | 1 μL |
| Vector | 2000 ng |
| Supplementing double distilled water to | 100 μL |

The reaction system was placed in a 37° C. incubator for enzyme cutting overnight.

Further, the linearized vector was recovered by an ultra-thin DNA product purification kit.

Further, the PCR product and linearized vector were recombined by using a ClonExpress® II One Step Cloning Kit.

Further, a recombinant product was transformed and entered into *E. coli* strain DH5α. After overnight growth on a plate, monoclones were selected for colony PCR identification and positive transformants were screened.

Further, whether the PCR fragment was successfully constructed was confirmed by a method of a Sanger sequencing. The final plasmid was pVF-SFT-SP.

(3) Construction of a Negative Control Plasmid pVSe

The primers used are as follows:

VSE F:
5'-ATGGCATGCCTGCAGACTAGTGAGACCGTGTAAGAGGTCTCG-3', SEQ ID NO. 29;

VSE R:
5'-GGCCAGTTAACGCTAGCGAATCGAGACCTCTTACACGGTCTC-3', SEQ ID NO. 30.

Referring to the authorized patent CN113215145A, an annealed product is prepared through fragment annealing, and then recombined and transformed.

(4) *Agrobacterium* Infection

The pVF-SFT and pVF-SFT-SP plasmids were transformed into *Agrobacterium* GV3101 through heat shock transformation.

Further, after the plate grew on kana and rifampicin double-resistant plates for two days, monoclones were selected for colony PCR identification and positive transformants were screened.

Further, positive monoclones were selected and shook overnight until the OD value is 0.5-1.0.

Further, the bacteria solution was collected at the bottom of the centrifuge tube by centrifugalization at 6000 rpm for 10 minutes, a supernatant was discarded, and the mixture was adjusted with the resuspending solution till OD=0.5-1.0.

A formula of the resuspending solution is shown in Table 20.

TABLE 20

| Formula of resuspending solution | |
| --- | --- |
| Resuspending solution | 100 mL |
| MgCl2 (1M) | 1 mL |
| MES(0.5M) | 2 mL |
| AS (100 mM) | 200 µL |

Further, after standing for 3 hours in the dark, pores were punched to inject the resuspending solution to the back of the flat cotyledon of cotton at a cotyledonary stage.

Further, after being kept in the dark for 12 h, the mixture was cultured in a 28° C. culture room.

Further, phenotypic observation was conducted one month after injection, and RNA was extracted from new leaves, and the expression levels of SFT and SP were detected by fluorescence quantitative PCR. It could be seen from the test results that flower buds preferentially appeared in the infected plants in the VF-SFT group. Five weeks after injection, statistics showed that no flower buds appeared in the VSe control group, 42% of the plants in the VF-SFT group had flower buds, and 14% of the plants in the VF-SFT-SP group had flower buds.

It can be seen from the above that compared with the control group, SP was successfully silenced and SFT was successfully overexpressed. In general, the flowering effect induced by viruses in the VF-SFT group is better than that in the VF-SFT-SP group. The above results show that by using the simplified two-component viral vector to concatenate multiple A genome copies can achieve VIGS, VOX, and VIF simultaneously. The experimental results in one month after injection are shown in Table 21.

TABLE 21

Experimental results of fluorescence quantitative PCR

| | SP expression level | Standard mean deviation |
| --- | --- | --- |
| VSe group | 0.977 | 0.091 |
| VF-SFT-SP group | 0.382 | 0.155 |

| | SFT gene expression (Log2) | Standard mean deviation |
| --- | --- | --- |
| VSe group | 0.986 | 0.399 |
| VF-SFT-SP group | 2374.835 | 57.413 |

Example 4

Simultaneous construction of two VIGS plasmids of simplified two-component viral vector from a single PCR product In this example, primers containing adapter sequences on both sides of the vector's multiple cloning site were designed, and partial fragments of a target gene GhOMT1 to be silenced were amplified by PCR. This PCR product could be used to construct the VIGS plasmids of two viruses at the same time.

A specific implementation process is briefly introduced below.

(1) Construction of Two Plasmids, pVS GhOMT1 and pVS2 GhOMT1

The primers used are as follows:

VS GhOMT1 F2:
5'-GGCCAGTTAACGCTAGCGAATTGTTGCACCATGACCAAGTCTT
CA-3', SEQ ID NO. 33;

VS GhOMT1 R2:
5'-ATGGCATGCCTGCAGACTAGTTGATGCCCTTGATTTGAGGATAC
TTTG-3', SEQ ID NO. 34;

The PCR reaction system is shown in Table 22, and the PCR amplification program is shown in Table 23.

TABLE 22

| PCR reaction system | |
| --- | --- |
| Component | Volume |
| Phanta Max Super-Fidelity DNA Polymerase | 1 µL |
| 2 × Phanta Max Buffer | 10 µL |
| dNTP Mix | 0.5 µL |
| Upstream primer | 0.8 µL |
| Downstream primer | 0.8 µL |
| Template DNA | 1 µL |
| Supplementing double distilled water to | 20 µL |

TABLE 23

| PCR amplification program | | | |
| --- | --- | --- | --- |
| Step | Temperature | Time | Cycle number |
| Predenaturation | 95° C. | 5 min | 1 |
| Denaturation | 95° C. | 15 sec | 33 |
| Annealing | 58° C. | 15 sec | |
| Extension | 72° C. | 1 min | |
| Extension | 72° C. | 5 min | 1 |

The amplified PCR products were recovered by using an agarose gel DNA recovery kit (enhanced type).

The pVS and pVS2 vectors were linearized by using a restriction enzyme BsaI.

An enzyme cutting system is shown in Table 24.

TABLE 24

| Enzyme cutting system | |
| --- | --- |
| Component | Volume |
| 10 × Cut smart buffer | 10 µL |
| BsaI | 1 µL |

TABLE 24-continued

| Enzyme cutting system | |
| --- | --- |
| Component | Volume |
| Vector | 2000 ng |
| Supplementing double distilled water to | 100 μL |

The reaction system was placed in a 37° C. incubator for enzyme cutting overnight.

Further, the linearized vector was recovered by an ultra-thin DNA product purification kit.

Further, the PCR product and linearized vector were recombined by using a ClonExpress® II One Step Cloning Kit.

Further, recombinant products of pVS-GhOMT1 and pVS2-GhOMT1 were transformed and entered into E. coli strains DH5α and EPI300 respectively. After overnight growth on a plate, four monoclones were selected for colony PCR identification and positive transformants were screened.

Further, whether the PCR fragment was successfully constructed was confirmed by a method of a Sanger sequencing.

As shown in FIG. 5, PCR identification results of a bacteria solution show that all eight single clone bands are correct. Sanger sequencing results also confirm that GhOMT1 is successfully constructed into two viral plasmids, pVS and pVS2. This shows that through the use of adapter sequences, the present disclosure can simply and quickly construct VIGS vectors for multiple viruses of one gene through the single PCR product. In the future, through the simplified construction method and the use of the adapters in the present disclosure, more different viral vectors can be expanded for the rapid construction of multiple viral plasmids of single genes.

The above is merely preferred embodiments of the present disclosure. It should be noted that those skilled in the art can further make several improvements and modifications without departing from the principle of the present disclosure. The improvements and modifications shall also be regarded as the scope of protection of the present disclosure.

```
                           Sequence table

<110> Cotton Research Institute, Chinese Academy of Agricultural Sciences
Sanya National Institute of Southern Propaganda, Chinese Academy of Agricultural
Sciences <120> A method for simply constructing two-component viral vector and related
applications thereof <141> 2023-11-14
<160> 34
<170> SIPOSequenceListing 1.0

<210> 2
<211> 30
<212> DNA
<213> Artificial Sequence
<400> 2
ggaaagacac cttttcgacc tttttcccct       30

<210> 3
<211> 33
<212> DNA
<213> Artificial Sequence
<400> 3
aaaaggtgtc tttcctgtgg atagcacgta cat       33

<210> 4
<211> 36
<212> DNA
<213> Artificial Sequence
<400> 4
taattcgggg atagcccttt ggtcttctga gactgt       36

<210> 5
<211> 37
<212> DNA
<213> Artificial Sequence
<400> 5
caaagggcta tccccgaatt aattcggcgt taattca       37

<210> 6
<211> 36
<212> DNA
<213> Artificial Sequence
<400> 6
aacgctagcg aattcactag tgcctgaaga ctggag       36

<210> 7
<211> 34
<212> DNA
<213> Artificial Sequence
<400> 7
```

```
-continued
```

| Sequence table |
|---|
| ggcatgcctg cagactagtg ctttactctg atcc 34 |

<210> 8
<211> 41
<212> DNA
<213> Artificial Sequence
<400> 8
aacctatccc aagtggagct ccgggggatc cactagtaaa c 41

<210> 9
<211> 41
<212> DNA
<213> Artificial Sequence
<400> 9
catgattacg aattcgagct cattcgagct ccagaacgat c 41

<210> 9
<211> 1473
<212> DNA
<213> Artificial Sequence
<400> 9

| | |
|---|---|
| gttattgctt ttagatagag ttcctgctct gcaagaggtg gatgacatcg gtggtcaatg | 60 |
| gtcgttttgg gtaactagag gtgagaaaag gattcattcc tgttgtccaa atctagatat | 120 |
| tcggggatgat cagagagaaa tttctcgaca gatatttctt actgctattg gtgatcaagc | 180 |
| tagaagtggt aagagacaga tgtcggagaa tgagctgtgg atgtatgacc aatttcgtga | 240 |
| aaatattgct gcgcctaacg cggttaggtg caataataca tatcagggtt gtacatgtag | 300 |
| gggtttttct gatggtaaga agaaaggcgc gcagtatgcg atagctcttc acagcctgta | 360 |
| tgacttcaag ttgaaagact tgatgctac tatggttagg aagaaaacta aagtggttca | 420 |
| tgctgctatg ctttttgctc ctgaaagtat gttagtggac gaaggtccat taccttctgt | 480 |
| tgacggttac tacatgaaga agaacgggaa gatctatttc ggttttgaga agatccttc | 540 |
| ctttttcttac attcatgact gggaagagta caagaagtat ctactgggga agccagtgag | 600 |
| ttaccaaggg aatgtgttct acttcgaacc gtggcaggtg agaggagaca caatgctttt | 660 |
| ttcgatctac aggatagctg gagttccgag gaggtcgcta tcatcgcaag agtactaccg | 720 |
| aagaatat atcagtagat gggaaaacat ggtgttgtc ccaatttcg atctggtcga | 780 |
| atcaacgcga gagttggtca agaaagacct gtttgtagag aaacaattca tggacaagtg | 840 |
| tttggattac atagctaggt tatctgacca gcagctgacc ataagcaatg ttaaatcata | 900 |
| cttgagttca aataattggg tcttattcat aaacgggcg gccgtgaaga acaagcaaag | 960 |
| tgtagattct cgagatttac agttgttggc tcaaactttg ctagtgaagg aacaagtggc | 1020 |
| gcgacctgtc atgaggggagt tgcgtgaagc aattctgact gagacgaaac ctatcacgtc | 1080 |
| attgactgat gtgctgggtt taatatcaag aaaactgtgg aagcagtttg ctaacaagat | 1140 |
| cgcagtcggc ggattcgttg gcatggttgg tactctaatt ggattctatc caagaaggt | 1200 |
| actaacctgg gcgaaggaca caccaaatg tccagaacta tgttacgaga actcgcacaa | 1260 |
| aaccaaggtg atagtatttc tgagtgttgt gtatgccatt ggaggaatca cgcttatgcg | 1320 |
| tcgagacatc cgagatggac tggtgaaaaa actatgtgat atgtttgata tcaaacgggg | 1380 |
| ggcccatgtc ttagacgttg agaatccgtg ccgctatatt gaaatcaacg atttctttag | 1440 |
| agtctgtatt cggcatctga gtccggtgag acg | 1473 |

<210> 10
<211> 107
<212> DNA
<213> Artificial Sequence
<400> 10
tgccgcgctt acgaaggcgg ctttggcaag attttttgtt actgagacgg tcttatgacg 60
gtttcggtct aggtttgatg tctttagaca tcatgaaggg ccttgcg 107

<210> 11
<211> 145
<212>DNA
<213> Artificial Sequence
<400> 11
gccgaagtat tttcacagaa gaagagaaac tgtcctaaat catgttggtg ggaagaagag 60
tgaacacaag ttagacgttt ttgaccaaag ggattacaaa atgattaaat cttacgcgtt 120
tctaaagata gtaggtgtac aattg 145

<210> 12
<211> 242
<212> DNA
<213> Artificial Sequence
<400> 12
ggatcccagg aaacagctat gaccaattcc cgatctagta acatagatga caccgcgcgc 60
gataatttat cctagtgaga ccgtaggtct cattctactg cgatcactga catacccag 120
ccagggcaac accataggtg caatgtttta tcctctccaa atgaaatgaa cttccttata 180
tagaggaagg gtcttgcgaa ggtagtggg attgtgcgtc atcccttacg tcagtggaga 240
tg 242

<210> 13
<211> 38

Sequence table

```
<212> DNA
<213> Artificial Sequence
<400> 13
ctttggaaga agacttgtac acttattaca aattcgat       38

<210> 14
<211> 43
<212> DNA
<213> Artificial Sequence
<400> 14
tccttaaatc cctaaagctt gggattagga cgtatcggac ctc  43

<210> 15
<211> 35
<212> DNA
<213> Artificial Sequence
<400> 15
aagctttagg gatttaagga cgtgaactct gttga           35

<210> 16
<211> 53
<212> DNA
<213> Artificial Sequence
<400> 16
attcgctagc gttaactggc caattcggta accttaactca cagaatctaa gtc  53

<210> 17
<211> 50
<212> DNA
<213> Artificial Sequence
<400> 17
gccagttaac gctagcgaat cgagaccgcc ctttgtgcat cttcatttcc       50

<210> 18
<211> 70
<212> DNA
<213> Artificial Sequence
<400> 18
gggacatgcc cgggcctcga atggcatgcc tgcagactag ttgagaccat taacaccgtt  60
gcggctaagc                                                         70

<210> 19
<211> 30
<212> DNA
<213> Artificial Sequence
<400> 19
tgtcagtgat cgcagtagaa tgtactaatt                30

<210> 20
<211> 26
<212> DNA
<213> Artificial Sequence
<400> 20
cgcgcgataa tttatcctag tttgcg                    26

<210> 21
<211> 49
<212> DNA
<213> Artificial Sequence
<400> 21
atggcatgcc tgcagactag tatgcctaga gatagagatc ctttggttg        49

<210> 22
<211> 41
<212> DNA
<213> Artificial Sequence
<400> 22
ggccagttaa cgctagcgaa ttcatgtcct acggccaccg g    41

<210> 23
<211> 44
<212> DNA
<213> Artificial Sequence
<400> 23
atggcatgcc tgcagactag tgcgtcttct agcagctgtt tccc  44

<210> 24
```

| Sequence table |
|---|
| <211> 48
<212> DNA
<213> Artificial Sequence
<400> 24
ggccagttaa cgctagcgaa tgagtgattg gggatgttat tgatgccc 48

<210> 25
<211> 44
<212> DNA
<213> Artificial Sequence
<400> 25
atggcatgcc tgcagactag tgcgtcttct agcagctgtt tccc 44

<210> 26
<211> 25
<212> DNA
<213> Artificial Sequence
<400> 26
ctaggctagt caggcgcaaa atgat 25

<210> 27
<211> 25
<212> DNA
<213> Artificial Sequence
<400> 27
atcattttgc gcctgactag cctag 25

<210> 28
<211> 41
<212> DNA
<213> Artificial Sequence
<400> 28
ggccagttaa cgctagcgaa ttcatgtcct acggccaccg g 41

<210> 29
<211> 42
<212> DNA
<213> Artificial Sequence
<400> 29
atggcatgcc tgcagactag tgagaccgtg taagaggtct cg 42

<210> 30
<211> 42
<212> DNA
<213> Artificial Sequence
<400> 30
ggccagttaa cgctagcgaa tcgagacctc ttacacggtc tc 42

<210> 31
<211> 21
<212> DNA
<213> Artificial Sequence
<400> 31
atggcatgcc tgcagactag t 21

<210> 32
<211> 21
<212> DNA
<213> Artificial Sequence
<400> 32
ggccagttaa cgctagcgaa t 21

<210> 33
<211> 45
<212> DNA
<213> Artificial Sequence
<400> 33
ggccagttaa cgctagcgaa ttgttgcacc atgaccaagt cttca 45

<210> 34
<211> 48
<212> DNA
<213> Artificial Sequence
<400> 34
atggcatgcc tgcagactag ttgatgccct tgatttgagg atactttg 48 |

SEQUENCE LISTING

```
Sequence total quantity: 34
SEQ ID NO: 1                moltype = DNA   length = 30
FEATURE                     Location/Qualifiers
source                      1..30
                            mol_type = other DNA
                            organism = synthetic construct
SEQUENCE: 1
ggaaagacac cttttcgacc tttttcccct                                          30

SEQ ID NO: 2                moltype = DNA   length = 33
FEATURE                     Location/Qualifiers
source                      1..33
                            mol_type = other DNA
                            organism = synthetic construct
SEQUENCE: 2
aaaaggtgtc tttcctgtgg atagcacgta cat                                      33

SEQ ID NO: 3                moltype = DNA   length = 36
FEATURE                     Location/Qualifiers
source                      1..36
                            mol_type = other DNA
                            organism = synthetic construct
SEQUENCE: 3
taattcgggg atagcccttt ggtcttctga gactgt                                   36

SEQ ID NO: 4                moltype = DNA   length = 37
FEATURE                     Location/Qualifiers
source                      1..37
                            mol_type = other DNA
                            organism = synthetic construct
SEQUENCE: 4
caaagggcta tccccgaatt aattcggcgt taattca                                  37

SEQ ID NO: 5                moltype = DNA   length = 36
FEATURE                     Location/Qualifiers
source                      1..36
                            mol_type = other DNA
                            organism = synthetic construct
SEQUENCE: 5
aacgctagcg aattcactag tgcctgaaga ctggag                                   36

SEQ ID NO: 6                moltype = DNA   length = 34
FEATURE                     Location/Qualifiers
source                      1..34
                            mol_type = other DNA
                            organism = synthetic construct
SEQUENCE: 6
ggcatgcctg cagactagtg ctttactctg atcc                                     34

SEQ ID NO: 7                moltype = DNA   length = 41
FEATURE                     Location/Qualifiers
source                      1..41
                            mol_type = other DNA
                            organism = synthetic construct
SEQUENCE: 7
aacctatccc aagtggagct ccgggggatc cactagtaaa c                             41

SEQ ID NO: 8                moltype = DNA   length = 41
FEATURE                     Location/Qualifiers
source                      1..41
                            mol_type = other DNA
                            organism = synthetic construct
SEQUENCE: 8
catgattacg aattcgagct cattcgagct ccagaacgat c                             41

SEQ ID NO: 9                moltype = DNA   length = 1474
FEATURE                     Location/Qualifiers
source                      1..1474
                            mol_type = other DNA
                            organism = synthetic construct
SEQUENCE: 9
gttattgctt ttagatagag ttcctgctct gcaagaggtg gatgacatcg gtggtcaatg         60
gtcgttttgg gtaactagag gtgagaaaag gattcattcc tgttgtccaa atctagatat        120
tcgggatgat cagagagaaa tttctcgaca gatatttctt actgctattg gtgatcaagc        180
tagaagtggt aagagacaga gtgtcggaga tgagctgtgg atgtatgacc aatttcgtga        240
aaatattgct gcgcctaacg cggttaggtg caataataca tatcagggtt gtacatgtag        300
gggttttttc tgatggtaaga agaaaggcgc gcagtatgcg atagctcttc acagcctgta        360
tgacttcaag ttgaaagact tgatggctac tatggttgag aagaaaacta agtggttca         420
```

```
tgctgctatg cttttttgctc ctgaaagtat gttagtggac gaaggtccat taccttctgt  480
tgacggttac tacatgaaga agaacgggaa gatctatttc ggttttgaga aagatccttc  540
cttttcttac attcatgact gggaagagta caagaagtat ctactgggga agccagtgag  600
ttaccaaggg aatgtgttct acttcgaacc gtggcaggtg agaggagaca caatgctttt  660
ttcgatctac aggatagctg gagttccgag gaggtcgtca tcatcgcaag agtactaccg  720
aagaatatat atcagtagat gggaaaacat ggttgttgtc ccaattttcg atctggtcga  780
atcaacgcga gagttggtca agaaaagacct gtttgtagag aaacaattca tggacaagtg  840
tttggattac atagctaggt tatctgacca gcagctgacc ataagcaatg ttaaatcata  900
cttgagttca aataattggg tcttattcat aaacggggcg gccgtgaaga acaagcaaag  960
tgtagattct cgagatttac agttgttggc tcaaacttg ctagtgaagg aacaagtggc 1020
gcgacctgtc atgagggagt tgcgtgaagc aattctgact gagacgaaac ctatcacgtc 1080
attgactgat gtgctgggtt taatatcaag aaaactgtgg aagcagtttg ctaacaagat 1140
cgcagtcggc ggattcgttg gcatggttgg tactctaatt ggattctatc caagaaaggt 1200
actaacctgg gcgaaggaca caccaaatgg tccagaacta tgttacgaga actcgcacaa 1260
aaccaaggtg atagtatttc tgagtgttgt gtatgccatt ggaggaatca cgcttatgcg 1320
tcgagacatc cgagatggac tggtgaaaaa actatgtgat atgtttgata tcaaacgggg 1380
ggcccatgtc ttagacgttg agaatccgtg ccgctattat gaaatcaacg atttctttag 1440
cagtctgtat tcggcatctg agtccggtga gacg                            1474

SEQ ID NO: 10           moltype = DNA   length = 107
FEATURE                 Location/Qualifiers
source                  1..107
                        mol_type = other DNA
                        organism = synthetic construct
SEQUENCE: 10
tgccgcgctt acgaaggcgg ctttggcaag atttttgtt actgagacgg tcttatgacg   60
gtttcggtct aggtttgatg tctttagaca tcatgaaggg ccttgcg              107

SEQ ID NO: 11           moltype = DNA   length = 145
FEATURE                 Location/Qualifiers
source                  1..145
                        mol_type = other DNA
                        organism = synthetic construct
SEQUENCE: 11
gccgaagtat tttcacagaa gaagagaaac tgtcctaaat catgttggtg ggaagaagag   60
tgaacacaag ttagacgttt ttgaccaaag ggattacaaa atgattaaat cttacgcgtt  120
tctaaagata gtaggtgtac aattg                                       145

SEQ ID NO: 12           moltype = DNA   length = 242
FEATURE                 Location/Qualifiers
source                  1..242
                        mol_type = other DNA
                        organism = synthetic construct
SEQUENCE: 12
ggatcccagg aaacagctat gaccaattcc cgatctagta acatagatga caccgcgcgc   60
gataatttat cctagtgaga ccgtaggtct cattctactg cgatcactga catacccag  120
ccagggcaac accataggtg caatgtttta tcctctccaa atgaaatgaa cttccttata  180
tagaggaagg gtccttgcgaa ggatagtggg attgtgcgtc atcccttacg tcagtggaga  240
tg                                                                242

SEQ ID NO: 13           moltype = DNA   length = 38
FEATURE                 Location/Qualifiers
source                  1..38
                        mol_type = other DNA
                        organism = synthetic construct
SEQUENCE: 13
ctttggaaga agacttgtac acttattaca aattcgat                          38

SEQ ID NO: 14           moltype = DNA   length = 43
FEATURE                 Location/Qualifiers
source                  1..43
                        mol_type = other DNA
                        organism = synthetic construct
SEQUENCE: 14
tccttaaatc cctaaagctt gggattagga cgtatcggac ctc                    43

SEQ ID NO: 15           moltype = DNA   length = 35
FEATURE                 Location/Qualifiers
source                  1..35
                        mol_type = other DNA
                        organism = synthetic construct
SEQUENCE: 15
aagctttagg gatttaagga cgtgaactct gttga                             35

SEQ ID NO: 16           moltype = DNA   length = 53
FEATURE                 Location/Qualifiers
source                  1..53
                        mol_type = other DNA
                        organism = synthetic construct
```

-continued

```
SEQUENCE: 16
attcgctagc gttaactggc caattcggta accttactca cagaatctaa gtc         53

SEQ ID NO: 17           moltype = DNA   length = 51
FEATURE                 Location/Qualifiers
source                  1..51
                        mol_type = other DNA
                        organism = synthetic construct
SEQUENCE: 17
gccagttaac gctagcgaat cgagaccgcc ctttgtgcat cttcatttcc t           51

SEQ ID NO: 18           moltype = DNA   length = 70
FEATURE                 Location/Qualifiers
source                  1..70
                        mol_type = other DNA
                        organism = synthetic construct
SEQUENCE: 18
gggacatgcc cgggcctcga atggcatgcc tgcagactag ttgagaccat taacaccgtt  60
gcggctaagc                                                         70

SEQ ID NO: 19           moltype = DNA   length = 30
FEATURE                 Location/Qualifiers
source                  1..30
                        mol_type = other DNA
                        organism = synthetic construct
SEQUENCE: 19
tgtcagtgat cgcagtagaa tgtactaatt                                   30

SEQ ID NO: 20           moltype = DNA   length = 26
FEATURE                 Location/Qualifiers
source                  1..26
                        mol_type = other DNA
                        organism = synthetic construct
SEQUENCE: 20
cgcgcgataa tttatcctag tttgcg                                       26

SEQ ID NO: 21           moltype = DNA   length = 49
FEATURE                 Location/Qualifiers
source                  1..49
                        mol_type = other DNA
                        organism = synthetic construct
SEQUENCE: 21
atggcatgcc tgcagactag tatgcctaga gatagagatc ctttggttg              49

SEQ ID NO: 22           moltype = DNA   length = 41
FEATURE                 Location/Qualifiers
source                  1..41
                        mol_type = other DNA
                        organism = synthetic construct
SEQUENCE: 22
ggccagttaa cgctagcgaa ttcatgtcct acggccaccg g                      41

SEQ ID NO: 23           moltype = DNA   length = 44
FEATURE                 Location/Qualifiers
source                  1..44
                        mol_type = other DNA
                        organism = synthetic construct
SEQUENCE: 23
atggcatgcc tgcagactag tgcgtcttct agcagctgtt tccc                   44

SEQ ID NO: 24           moltype = DNA   length = 48
FEATURE                 Location/Qualifiers
source                  1..48
                        mol_type = other DNA
                        organism = synthetic construct
SEQUENCE: 24
ggccagttaa cgctagcgaa tgagtgattg gggatgttat tgatgccc               48

SEQ ID NO: 25           moltype = DNA   length = 44
FEATURE                 Location/Qualifiers
source                  1..44
                        mol_type = other DNA
                        organism = synthetic construct
SEQUENCE: 25
atggcatgcc tgcagactag tgcgtcttct agcagctgtt tccc                   44

SEQ ID NO: 26           moltype = DNA   length = 25
FEATURE                 Location/Qualifiers
source                  1..25
```

```
                        mol_type = other DNA
                        organism = synthetic construct
SEQUENCE: 26
ctaggctagt caggcgcaaa atgat                                              25

SEQ ID NO: 27          moltype = DNA  length = 25
FEATURE                Location/Qualifiers
source                 1..25
                       mol_type = other DNA
                       organism = synthetic construct
SEQUENCE: 27
atcattttgc gcctgactag cctag                                              25

SEQ ID NO: 28          moltype = DNA  length = 41
FEATURE                Location/Qualifiers
source                 1..41
                       mol_type = other DNA
                       organism = synthetic construct
SEQUENCE: 28
ggccagttaa cgctagcgaa ttcatgtcct acggccaccg g                            41

SEQ ID NO: 29          moltype = DNA  length = 42
FEATURE                Location/Qualifiers
source                 1..42
                       mol_type = other DNA
                       organism = synthetic construct
SEQUENCE: 29
atggcatgcc tgcagactag tgagaccgtg taagaggtct cg                           42

SEQ ID NO: 30          moltype = DNA  length = 42
FEATURE                Location/Qualifiers
source                 1..42
                       mol_type = other DNA
                       organism = synthetic construct
SEQUENCE: 30
ggccagttaa cgctagcgaa tcgagacctc ttacacggtc tc                           42

SEQ ID NO: 31          moltype = DNA  length = 21
FEATURE                Location/Qualifiers
source                 1..21
                       mol_type = other DNA
                       organism = synthetic construct
SEQUENCE: 31
atggcatgcc tgcagactag t                                                  21

SEQ ID NO: 32          moltype = DNA  length = 21
FEATURE                Location/Qualifiers
source                 1..21
                       mol_type = other DNA
                       organism = synthetic construct
SEQUENCE: 32
ggccagttaa cgctagcgaa t                                                  21

SEQ ID NO: 33          moltype = DNA  length = 45
FEATURE                Location/Qualifiers
source                 1..45
                       mol_type = other DNA
                       organism = synthetic construct
SEQUENCE: 33
ggccagttaa cgctagcgaa ttgttgcacc atgaccaagt cttca                        45

SEQ ID NO: 34          moltype = DNA  length = 48
FEATURE                Location/Qualifiers
source                 1..48
                       mol_type = other DNA
                       organism = synthetic construct
SEQUENCE: 34
atggcatgcc tgcagactag ttgatgccct tgatttgagg atactttg                     48
```

The invention claimed is:

1. A method for simply constructing a two-component viral vector comprising a first genomic component and a second genomic component, the method comprising:
   modifying a restriction site within the multiple cloning site of the first genomic component into a new restriction site, modifying the flanking sites of the new restriction site into the adapter sequences set forth by SEQ ID NO: 31 and SEQ ID NO: 32, and concatenating the first genomic component via the adapter sequences through PCR and homologous recombination;
   ligating the concatenated first genomic component and the second genomic component into a plasmid to obtain a single plasmid encoding the two-component viral vector;

wherein the two-component viral vector is a two-component DNA or a two-component RNA viral vector;

when the two-component DNA viral vector is the cotton leaf crumple virus (CLCrV), the two genomic components are flanked by respective common regions (CRs), the plasmid is the *Agrobacterium* Ti plasmid, the CRs can be linked via a restriction site sequence, and the two genomic components are inserted between the T-DNA borders of the *Agrobacterium* Ti plasmid;

when the two-component RNA viral vector is the tobacco rattle virus (TRV), the two genomic components are placed in two separate expression cassettes for independent expression from the 35S promoter, wherein each expression cassette comprises the NOS terminator.

* * * * *